(12) United States Patent
Kober et al.

(10) Patent No.: US 7,967,968 B2
(45) Date of Patent: Jun. 28, 2011

(54) METHOD AND SYSTEM FOR MONITORING MATERIAL SEPARATION PROCESS SUCH AS ELECTROPHORESIS PROCESS IN A SAMPLE

(75) Inventors: Yoran Kober, Alona (IL); Meir Matana, Or-Yehuda (IL); Erez Kelly, Modean (IL)

(73) Assignee: D.N.R.-Imaging Systems Ltd., Matam, Haifa (IL)

( * ) Notice: Subject to any disclaimer, the term of this patent is extended or adjusted under 35 U.S.C. 154(b) by 1101 days.

(21) Appl. No.: 10/592,773

(22) PCT Filed: Mar. 15, 2005

(86) PCT No.: PCT/IL2005/000294
§ 371 (c)(1),
(2), (4) Date: Nov. 14, 2006

(87) PCT Pub. No.: WO2005/086586
PCT Pub. Date: Sep. 22, 2005

(65) Prior Publication Data
US 2008/0142365 A1    Jun. 19, 2008

(51) Int. Cl.
C25B 15/02 (2006.01)
B01D 61/46 (2006.01)
(52) U.S. Cl. .................... 204/607; 204/461; 204/612
(58) Field of Classification Search .................. 204/450, 204/600, 461, 612
See application file for complete search history.

(56) References Cited

U.S. PATENT DOCUMENTS

| 5,055,172 | A |   | 10/1991 | Cathel et al. |
|---|---|---|---|---|
| 5,104,512 | A | * | 4/1992 | Gombocz et al. ............. 204/607 |
| 5,120,419 | A |   | 6/1992 | Papp |
| 5,627,643 | A |   | 5/1997 | Birnbaum et al. |
| 5,976,338 | A |   | 11/1999 | Fujita et al. |
| 6,005,663 | A |   | 12/1999 | Waterhouse et al. |
| 6,090,545 | A |   | 7/2000 | Wohlstadter et al. |
| 6,103,479 | A |   | 8/2000 | Taylor |
| 2002/0162745 | A1 | * | 11/2002 | Nordman et al. ............. 204/452 |
| 2002/0195342 | A1 |   | 12/2002 | Lee et al. |
| 2003/0013126 | A1 |   | 1/2003 | Singh et al. |

FOREIGN PATENT DOCUMENTS

| EP | 0 330 897 A2 | 9/1989 |
|---|---|---|
| EP | 0 457 526 A2 | 11/1991 |
| EP | 0 911 630 A1 | 4/1999 |
| JP | 1-195357 A | 8/1989 |
| JP | 2000-146910 A | 5/2000 |
| WO | WO 97/27331 A2 | 7/1997 |
| WO | WO 98/08978 A1 | 3/1998 |
| WO | WO 01/06247 A1 | 1/2001 |
| WO | 02/33392 A2 | 4/2002 |

* cited by examiner

*Primary Examiner* — Ula C Ruddock
*Assistant Examiner* — J. Christopher Ball
(74) *Attorney, Agent, or Firm* — The Nath Law Group; Susanne M. Hopkins; Ari G. Zytcer

(57) ABSTRACT

A method and system are presented for use in analyzing a sample. The method comprises applying real time monitoring to a sample while undergoing a separation process consisting of spatial separation of molecules of different molecular weights in the sample. The system includes a monitoring unit configured to be integrated with a separation unit in which the separation process takes place.

46 Claims, 11 Drawing Sheets

(GENERAL ART)

METHOD AND SYSTEM FOR MONITORING MATERIAL SEPARATION PROCESS SUCH AS ELECTROPHORESIS PROCESS IN A SAMPLE

This is a National Phase Application filed under 35 U.S.C. §371 as a national stage of PCT/IL2005/000294, filed on Mar. 15, 2005, an application claiming the benefit under 35 U.S.C. §119(e) of U.S. Provisional Application No. 60/577,581, filed on Jun. 8, 2004, and an application claiming the benefit under 35 U.S.C. §119 of Israeli Patent Application No. 160869, filed on Mar. 15, 2004, the content of each of which is hereby incorporated by reference in its entirety.

FIELD OF THE INVENTION

This invention relates to a method and system for monitoring material separation process, such as electrophoresis process, applied to a sample while in matrix medium and aimed at spatially separating molecules of different molecular weights contained in the sample.

BACKGROUND OF THE INVENTION

Various types of investigations of samples, e.g., biological samples, require spatial separation of different macromolecules of the sample from one another. This is typically conducted by applying to the sample an electrophoresis process in which different molecules are separated due to their different molecular weights.

FIG. 1 schematically illustrates the principles of this conventional technique utilizing a gel electrophoresis system 1. The system 1 includes a container 3 in which the separation process takes place, and a voltage supply assembly 5. Container 3 is filled with an appropriate matrix medium 7, typically gel, e.g., polysaccharide such as Agarose. Several dozes of the same sample 9 (or different samples, as the case may be), composed of different molecules to be separated, are inserted into specific holes (wells) 11 in the gel medium 7. The molecules of the sample 9 may be naturally charged, charge may be applied prior to electrophoresis, or an additional ionic buffer serving as a separating agent may be added to the gel medium 7. Then, the voltage supply assembly 5 is operated to apply an electric potential (voltage difference) across the gel medium 7. The gel medium 7 acts as a sieving matrix to assist in retarding and separating the individual molecules as they migrate under the electric potential. The electric potential is typically applied for a certain fixed time period, during which the lighter molecules move more quickly, and at the end of this time period, the lighter molecules thus moved farther than heavier molecules.

In order to identify the results of the separation process, specific substances (markers) are typically applied to the sample 9 prior to the application of the electric potential. Such markers include for example fluorescent or chemiluscent materials, which are tied to specific molecules in the sample 9. After the application of electric potential is ceased, an exposure process commences to thereby image the sample and identify the molecules contained therein. This is typically carried out in a separate system (in 'dark' room), to which the sample is transferred from the separation system. During the imaging process, the separation results (gel 7 with the rest of the sample material in it) are 'exposed' to predetermined radiation, thus enabling visualization of the separation results. In a case of fluorescents dyes, this procedure includes application of UV illumination and consequent imaging of the gel medium 7. Once the image is ready, analysis can commence, for example aimed at identifying the molecules and determining their amount in the sample 9.

U.S. Pat. No. 5,055,172 discloses an electrophoresis system, which separates charged chemical substances by means of applying an electrical potential across a buffer solution which includes those chemical substances. The system includes a power supply and control system which has a wide dynamic range of constant voltage, current and power which may be supplied. The power supply includes a flyback topology and a control system which allows an operator to specify a wide range of constant voltage, current or power supply requirements for the electrophoresis system.

U.S. Pat. No. 5,976,338 discloses a DNA analyzer that comprises a pair of temperature control units on both sides of gel and a light-transmitting slit on one of the elements. Irradiation of an excitation beam over the gel and signal detection are practiced through the slit. By introducing dry air onto the slit part, mildew occurrence is prevented on the detecting part. The power level applied to the gel is detected, and the temperature of the temperature control units is calculated, so that the gel temperature might be a predetermined temperature. On the basis of the detected power level, the feedback control of the power level is thereafter carried out. The gel temperature can be controlled appropriately and strictly during electrophoresis in an automatic fluorescent electrophoresis system, so that high-speed analysis can be done highly reproducibly at a higher voltage applied even by SSCP.

SUMMARY OF THE INVENTION

There is a need in the art to facilitate analysis of a sample undergoing a separation process, as well as to enable monitoring of the separation process itself, by providing a novel method and system enabling real-time monitoring of the separation process and the separation results.

The main idea of the present invention is associated with the following. Electrophoresis (generally, a separation process) is a complex process. If any of the operational parameters of this process exceeds or does not reach a certain value, the separation process may fail. For example, if the intensity of the applied electric field is too high and/or the duration of the application of an electric filed is too long, lighter molecules may proceed too far along the gel and exit the other side of the gel, and thus cannot be identified during imaging. With the conventional electrophoresis systems, such unwanted results can be detected only after cessation of the applied electric field. With lack of appropriate information as to optimal operational parameters, it therefore enforces the system operator to operate an electrophoresis system or according to inaccurate rules of the thumb or in cycles. With respect to the latter option, the operator is enforced to shorten the duration and/or intensity of the applied electric field. The operator stops the process, and transfers the container with the sample embedded in a matrix medium to a 'dark' room to visualize the separation results. If molecules advancement along the matrix medium is not sufficient, the operator re-applies the electric field for additional unknown a-priori duration or change in the intensity of the applied field. In such a way the operator should continue until and if he is satisfied with the results. It is evident, that the resultant separation process is inefficient, and time and chemical consuming. Moreover, lots of data cannot be obtained due to such posterior monitoring.

The present invention solves the above problems by providing a monitoring method and system enabling real time monitoring of the separation process.

For the purpose of this invention, the term "separation process" signifies any process in which molecules are spatially separated from each other. Such separation may be various types of electrophoresis such as gel- and capillary-electrophoresis, and gel chromatography. However, the embodiments will be mainly exemplified with respect to gel electrophoresis.

The term "imaging" used herein signifies image acquisition of a medium under investigation (sample in matrix medium) by an imaging detector and/or direct visualization (observation) of the medium by user.

Thus, according to one aspect of the invention, there is provided a method for use in analyzing a sample, the method comprising: applying real time monitoring to a sample while undergoing a separation process consisting of spatial separation of molecules of different molecular weights in the sample.

It should be understood that the phrase "while undergoing a separation process" used herein signifies that the sample is under the conditions of the separation process (namely, located within the separation process environment) and is not handled to another place for the monitoring purposes, while the separation process itself might not proceed during the monitoring.

The monitoring may be applied continuously when the separation process proceeds, or in timely separated sessions. The duration of the time session may be defined by parameters of the sample and/or a matrix medium in which the sample is embedded, and/or defined by parameters of the separation process.

The monitoring may be applied (continuously or in timely separated sessions) during a predetermined time period of the separation process. This predetermined time period may be defined so as to identify a certain molecules type in the sample, and/or defined by parameters of the sample and/or a matrix medium in which the sample is embedded, and/or defined by parameters of the separation process.

The results of said monitoring are analyzed to thereby enable controlling the separation process.

The monitoring consists of exciting the medium (the matrix medium containing the sample) with an external exciting field and detecting a response of the excited region to this external exciting field. The external exciting field may be selected so as to enable excitation of a specific molecule in the sample. The monitoring may include providing data regarding an optimal duration of the separation process, thereby enabling to stop the separation or allow proceeding thereof dependent on the monitoring results; and/or providing data regarding optimal parameters of the separation process, thereby allowing for varying the separation process parameters. The parameters of the separation process that are to be controlled include a parameter of an external field commencing the separation process. Considering the electrophoresis process, this external field is a voltage applied across a matrix medium in which the sample is embedded, and the process parameters to be controlled include the voltage supply value and/or a direction of the electric field through the medium.

The monitoring may include measuring a temperature condition and/or humidity condition of a matrix medium in which the sample is embedded.

The real time monitoring is achieved by using a monitoring unit configured to be integrated with a separation unit, in which the separation process takes place. Such a separation unit includes a container for carrying the sample embedded in the matrix medium, and a source of an external field commencing the separation process.

The monitoring consists of imaging a medium in the separation unit (matrix medium carrying the sample). As indicated above, this may be image acquisition using an imaging detector, and/or visual observation of the medium by user. The imaging thus may comprise irradiating the medium by exciting radiation of at least one predetermined wavelength range, and detecting a radiation response of the medium.

The method of the invention preferably also provides for carrying out public collection of data, analyzing the public collection data and also data indicative of the monitoring results, and generating analyzed data indicative of this analysis. This analyzed data is preferably stored and used to create a library.

According to another aspect of the invention, there is provided a method for use in analyzing a sample contained in a matrix medium, the method comprising: commencing a separation process in the sample consisting of spatial separation of molecules of different molecular weights in the sample; and applying a monitoring process to the sample while undergoing the separation process.

According to yet another aspect of the invention, there is provided a method for use in analyzing a sample contained in a matrix medium, the method comprising: providing a monitoring system configured to be integrated with a separation unit, which includes a container containing a sample embedded in a matrix medium and a source of an external field capable of inducing a separation process in the sample consisting of spatial separation of molecules of different molecular weights in the sample, the method thereby enabling real time controlling of the separation process and real time analyzing of the separation results.

According to yet another aspect of the invention, there is provided a method for use in analyzing a separation process to be applied to a sample and consisting of spatial separation of molecules of different molecular weights in the sample, the method comprising establishing a library including information regarding various parameters of the separation process and media used therein, thereby enabling using said library for monitoring and affecting performance of the separation process.

The establishing of the library includes: searching and collecting public data about separation processes; collecting data resulted from real time monitoring separation processes; sorting and analyzing the collected data and generating analyzed data indicative thereof; and storing said analyzed data. The data about the separation processes preferably also includes data about devices and materials used therein.

According to yet another aspect of the invention, there is provided a system for use in analyzing a sample, the system comprising: a separation unit including a container for carrying a matrix medium for a sample to be embedded therein, and a source of an external field configured and operable to commence a separation process consisting of spatial separation of molecules of different molecular weights in the sample; and a monitoring unit configured to be integrated with said separation unit, the system thereby enabling real time monitoring of the separation process and the separation results.

The monitoring unit is configured to be attachable to the separation unit, or to be mountable on the separation unit, or to incorporate the separation unit thereinside. The monitoring unit comprises an excitation unit configured to generate an exciting field to be applied to a substance in the separation unit to thereby cause a response of the substance to the exciting field; and preferably also comprises a detection unit configured to detect the response and generate data indicative thereof. The detection unit is preferably shiftable between its operative position being in the optical path of the radiation response and an inoperative position being outside the radiation response path. When in the inoperative position of the detection unit, visual observation of the sample may be carried out, in which case a spectral filter is used (configured to block UV radiation and transmit all other spectral components). Such a spectral filter would thus be shiftable between its operative and inoperative positions (like a shutter) to be selectively operated. It should be understood that the system may be configured to enable concurrent image acquisition and visual observation. This may be implemented by using a beam splitting means (such as a pinhole) in the optical path of the radiation response coming from the medium.

The monitoring unit includes a housing configured to provide a dark room environment for the sample located therein.

The system preferably also includes a control unit connectable at least to the monitoring unit and operable to receive and process data indicative of the monitoring results. The control unit may also be connectable to the separation unit to affect operation of the separation unit based on the processing results.

In a preferred embodiment, the monitoring unit is a two-part unit: one part carries the excitation unit and is mountable at one side of the separation unit, and the other part carries the detection unit and is mountable at the opposite side of the separation unit.

According to yet another aspect of the invention, there is provided a monitoring system comprising a source of exciting field to be applied to a medium to cause a response of the medium to said exciting field, and a detection unit for detecting the response and generating data indicative thereof, the system being configured for integrating it with a separation unit, which includes a container for carrying a matrix medium for a sample to be embedded therein, and includes a source of an external field of the kind capable of commencing a separation process consisting of spatial separation of molecules of different molecular weights in the sample, the monitoring system thereby enabling real time monitoring of the separation process and the separation results.

According to yet another aspect of the invention, there is provided a monitoring system including a source of exciting field to be applied to a medium to cause a response of the medium to said exciting field, and a detection unit for detecting the response and generating data indicative thereof, the system being configured to provide a dark room environment thereinside and being configured for integrating the system with a separation unit, which includes a container for carrying a matrix medium for a sample to be embedded therein, and includes a source of an external field of the kind capable of commencing a separation process consisting of spatial separation of molecules of different molecular weights in the sample, the monitoring system thereby enabling real time monitoring of the separation process and the separation results.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
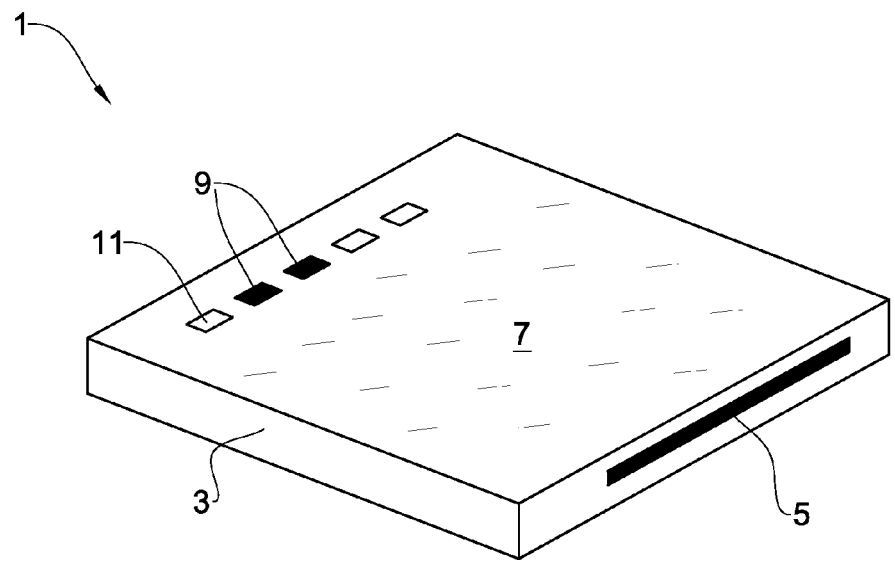
FIG. 1 schematically illustrates the principles of the conventional electrophoresis process.

FIG. 1 illustrates a conventional electrophoresis system. The electrophoresis system is configured to apply an electric field across a matrix medium containing a sample to thereby commence spatial separation of molecules of the sample having different molecular weights.

Reference is made to FIGS. 2A to 2D, exemplifying a monitoring system 10 according to the invention. The monitoring system 10 includes a monitoring unit 14 that is configured so as to be integrated with a separation unit 12. The separation unit 12 is configured to support a sample and to commence the separation process therein, which separation process consists of spatial separation of molecules of different molecular weights in the sample. The separation unit 12 may generally be constructed as the system of FIG. 1. Preferably, the separation unit 12 utilizes container 12A in the form of a closed cassette in which a matrix medium (gel) is enclosed, e.g., the disposable cassette E-Gel® (commercially available from Invitrogen® of Carlsbad, Calif. The cassette is preferably substantially flat, and has at least its bottom and top walls made of a material transparent with respect to predetermined radiation, e.g., UV transparent material. Also provided in the separation unit is an external field source (not shown here), e.g., electrodes arrangement and a voltage supply unit in the case of electrophoresis unit.

The monitoring unit 14 includes a housing 14A that is configured to be integrated with the separation unit 12, and that carries therein an excitation unit and a detection unit, as will be described further below. In the present example, the housing 14A of the monitoring unit 14 is configured to be mountable on (or attachable to) the separation unit 12. It should, however, be understood that the housing 14A may be configured to allow incorporation of the separation unit therein. For example, the housing 14A may be formed with an opening (slot) and a support stage thereinside allowing for receiving the separation unit and maintaining it on the support stage during the separation and analyzing processes. Generally, the monitoring unit 14 is configured and operable to implement real time monitoring of the separation process and the results of this process.

In the present example, the housing 14A of the monitoring unit 14 is a two-part assembly, configured for enclosing the separation unit 12 therebetween. The monitoring unit 14 includes an excitation unit 14B which in the present example is mounted in the lower part of the housing to be below the separation unit, and a detection unit (not shown here) located inside the upper part of the housing 14A to be above the separation unit. The housing 14A is configured to provide a "dark room" environment for the detection process. In the present example, the configuration is such that the excitation unit and the detection unit are located at opposite sides of the separation unit 12 thereby operating in the so-called "transmission mode", but is should be understood and will be described further below that the "reflection mode" operation is suitable as well.

Figure 2A:
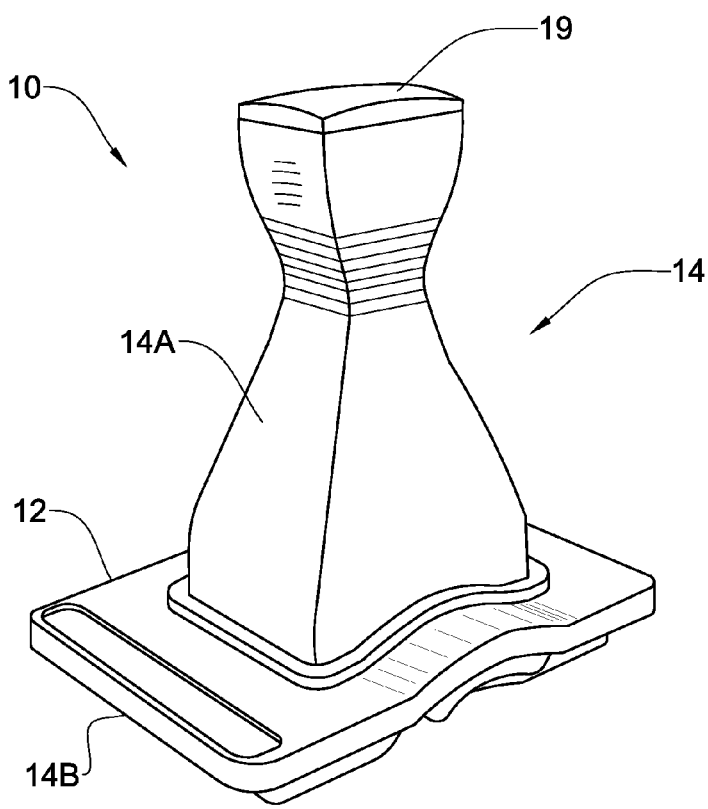
FIGS. 2A to 2D illustrate a specific, but non limiting example of a monitoring unit of the present invention.
Figure 2B:
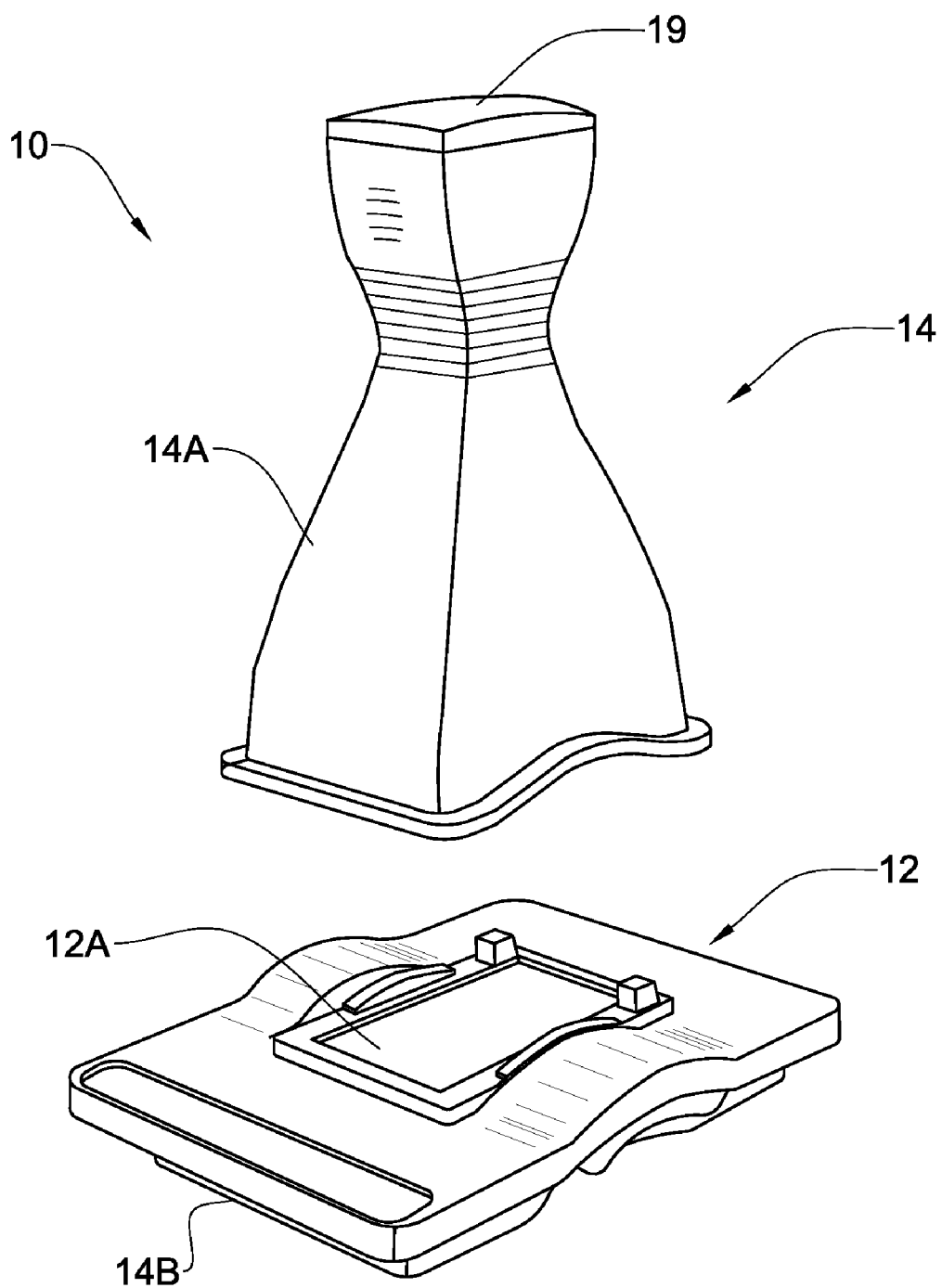
Figure 2C:
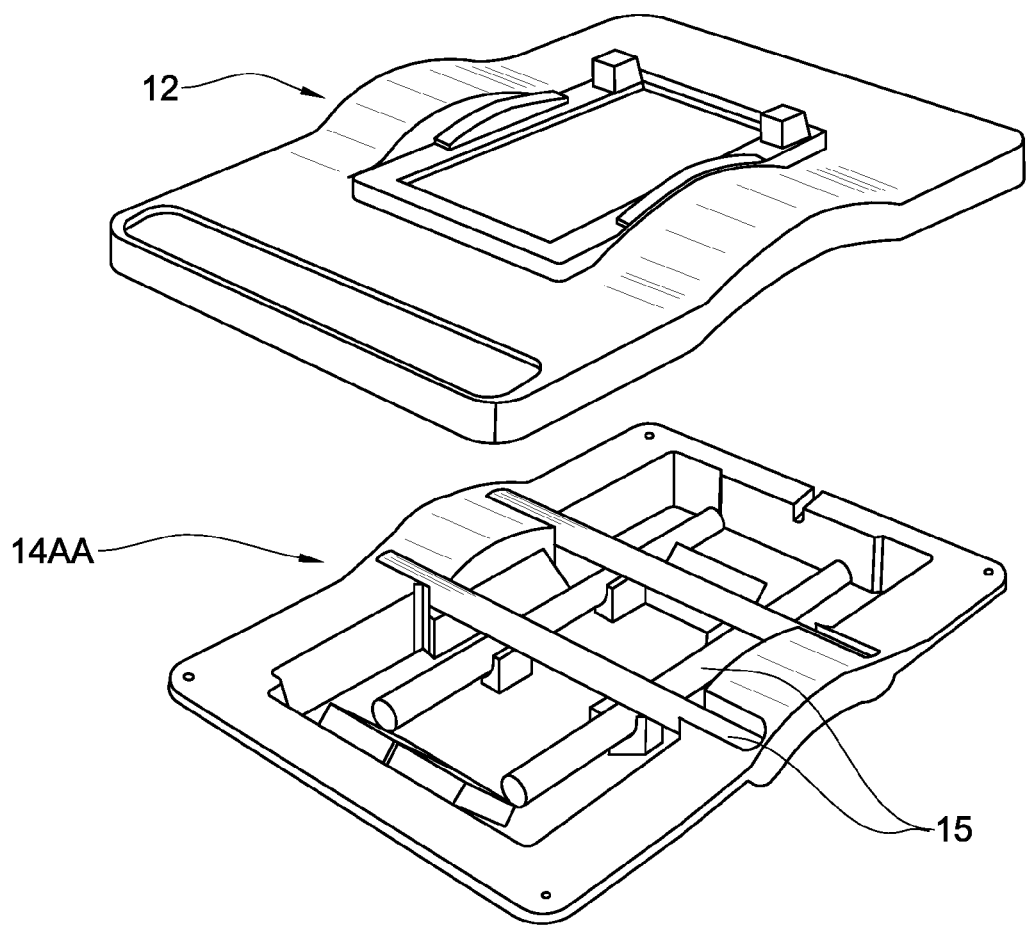
Figure 2D:
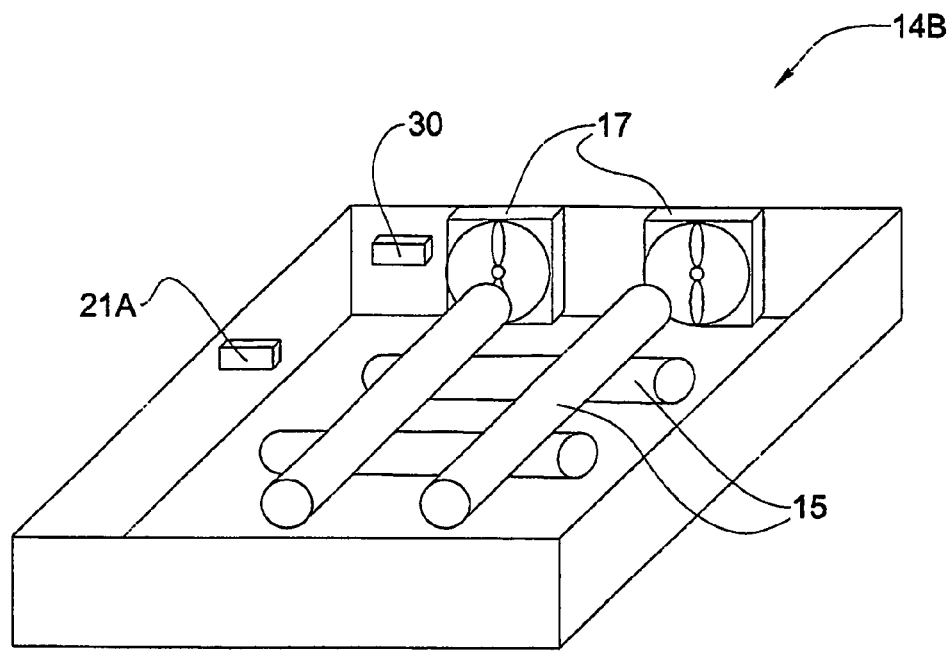

FIG. 2C presents the base of the system 10, opened into its two compartments—monitoring unit 14 (its excitation unit 1413) and separation unit 12. Generally, excitation unit 14B is configured and operable to generate an exciting field (e.g., electromagnetic radiation) to cause a response of materials in the container 12A to this exciting field. FIG. 2D more specifically illustrates the configuration of the excitation unit 14B In the present example, the excitation unit 14B includes four elongated UV lamps generally at 15, which are arranged in two perpendicular pairs. The UV radiation is directed to the container 12A by a back reflector (not shown) mounted under the excitation sources 15. Also included in the base part of the system 10 are ventilators 17 for cooling the matrix medium (gel) and/or the entire system 10 and environment sensor(s) 30, e.g., temperature sensor.

The monitoring system 10 also includes protection means for protecting a user from dangerous radiation or toxic substances or gases which may penetrate his respiratory system. To this end, the housing 14AA of the monitoring unit not only serves as "dark room" environment, but also prevents the arrival of such dangerous radiation to the user. The system 10 is provided with a mechanism that ensures appropriate accommodation of the housing 14AA above the separation unit 12 and enclosing an upper opening 19 in the housing 14AA Such a mechanism operates to automatically provide the operation of the monitoring system, only after the system is appropriately sealed. This mechanism can include a magnetic interlock composed of a magnetic field generator 21A mounted on the base of the housing 14AA and a magnetic sensor (not shown) mounted on the separation unit 12. The magnetic field can be sensed only when the housing of the monitoring unit is attached to the separation unit 12. Once this attachment is detected, a control unit (not shown here) actuates the operation of the monitoring unit 14.

Figure 2E:
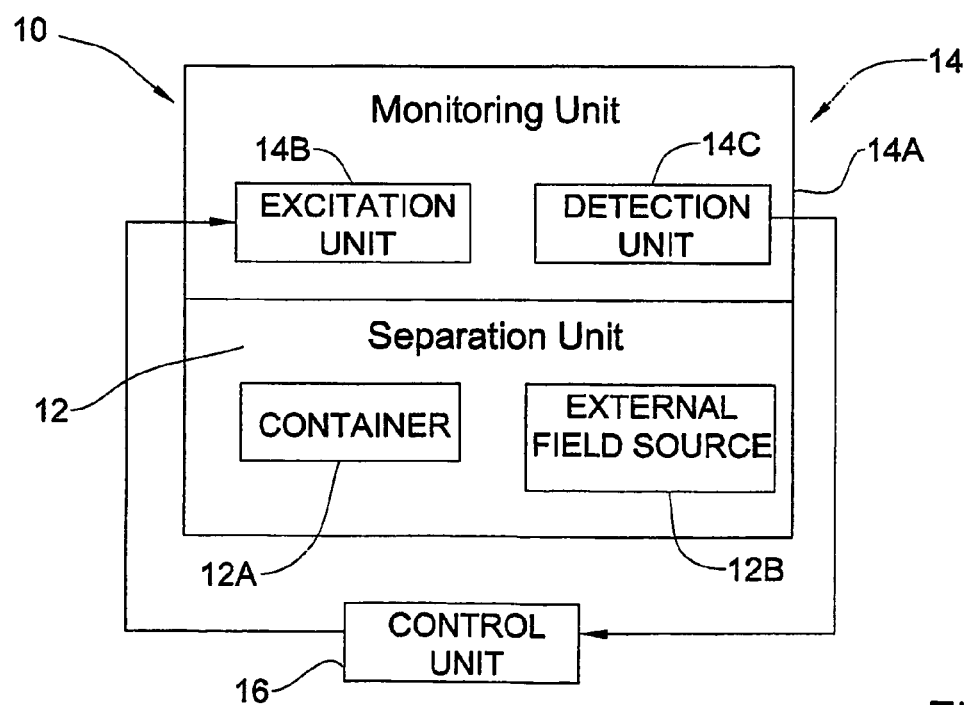
FIG. 2E is a block diagram of a system utilizing the monitoring unit of the present invention.

FIG. 2E illustrates, by way of a block diagram, the elements of the system 10. The monitoring unit 14 includes an excitation source 14B, and a detection unit 14C, and is associated with the separation unit 12. The separation unit 12 includes a container 12A for carrying a matrix medium for a sample to be introduced therein, and a source of an external field 12B of the kind capable of commencing the separation process in the sample. In the case of electrophoresis, this might be an electric field, applied across the container 12A along one axis (one-dimensional electrophoresis) or across two mutually perpendicular axes (two-dimensional electrophoresis). The container 12A being part of the separation unit 12 might be an open container (e.g., a bath) or a closed container (e.g., disposable cassette). The container 12A is filled with a matrix medium (e.g., gel, membranes, slides, plates, or extracted tissues).

As indicated above, the housing 14A of the monitoring unit is configured to prevent any penetration or emerging of signal in or from the monitoring unit. This is aimed at protecting the system operator as well as the sample in the separation unit 12, from damages caused by such signals. The excitation source 14B is configured and operable to generate an exciting field to thereby cause a response of the sample to this field. For example, the excitation source is a source of electromagnetic radiation to thereby cause a radiation response (emission) from materials in the container 12A of the separation unit 12. The electromagnetic radiation source may include lasers, diode lasers, LEDs, VCSELs, broadband sources, etc. These excitation sources are combined with appropriate optical means (e.g., free space propagation optics, fiber optics and waveguides) to convey the exciting radiation to the container 12A.

It should be noted that the monitoring unit 14 may include appropriate chemilfluoroscence or chemiluminance substance which upon contact with materials contained in container 12A, will effect emission from these materials or part thereof to be detected by a detector of the detection unit 14B. The radiation response may include visible flourochromes, fluorescence, chemiflourscence, chemiluminescence, chromatography, autoradiograms, visible light, NIR and IR absorption or emission, and Raman scattering.

The detection unit 14B is configured for detecting the response of the materials in the container to the exciting field (e.g., electromagnetic radiation response) and generating data indicative of the detected response; and/or for allowing visual observation of the materials in the container by user. The excitation/detection process may be aimed at monitoring the separation results and/or monitoring the condition of the separation process, e.g., the condition of the matrix medium (e.g., temperature, humidity). Also provided in the system 10 is a control unit 16 which may be a constructional part of the monitoring unit 14 or may be a stand-alone unit connectable (by wires or wireless) to the monitoring unit for receiving and processing data representative of the analyzing procedure, and possibly also connectable to the separation unit 12 for operating this unit. Preferably, the control unit 16 operates to control the operation of the overall integrated system including the separation and monitoring units 12 and 14, and also to perform the data processing according to predetermined algorithms. The control unit 16 is typically a computer system including a data input utility (e.g., keyboard, USB), a data output utility (display), and a data processing and analyzing utility. It should be noted that in order to allow the visual observation of the inside of the container, the detection unit 14C includes a tight cover made of UV blocking material (plastic) and transparent for other spectrum. The cover is mounted so as to be shiftable between its operative position being located in the optical path of the radiation response and inoperative position being outside this optical path. The magnetic interlock operates to turn the radiation source 15 on upon detecting that the cover is brought to its operative position, thus allowing the user to observe the materials in the container through the transparent plastic cover. Considering both the image acquisition mode and the visual observation mode, the imaging detector is preferably shiftable between its operative and inoperative positions, such that when the imaging detector is brought to its inoperative position, the UV blocking cover (filter) is brought to its operative position. Alternatively, the detection unit is configured to define an imaging channel and a visual channel for the radiation response propagation. This is implemented by using a beam splitting means, such as pinhole, that directs a part of the response to the imaging detector and reflects the other part of the response to the UV blocking cover.

Figure 3:
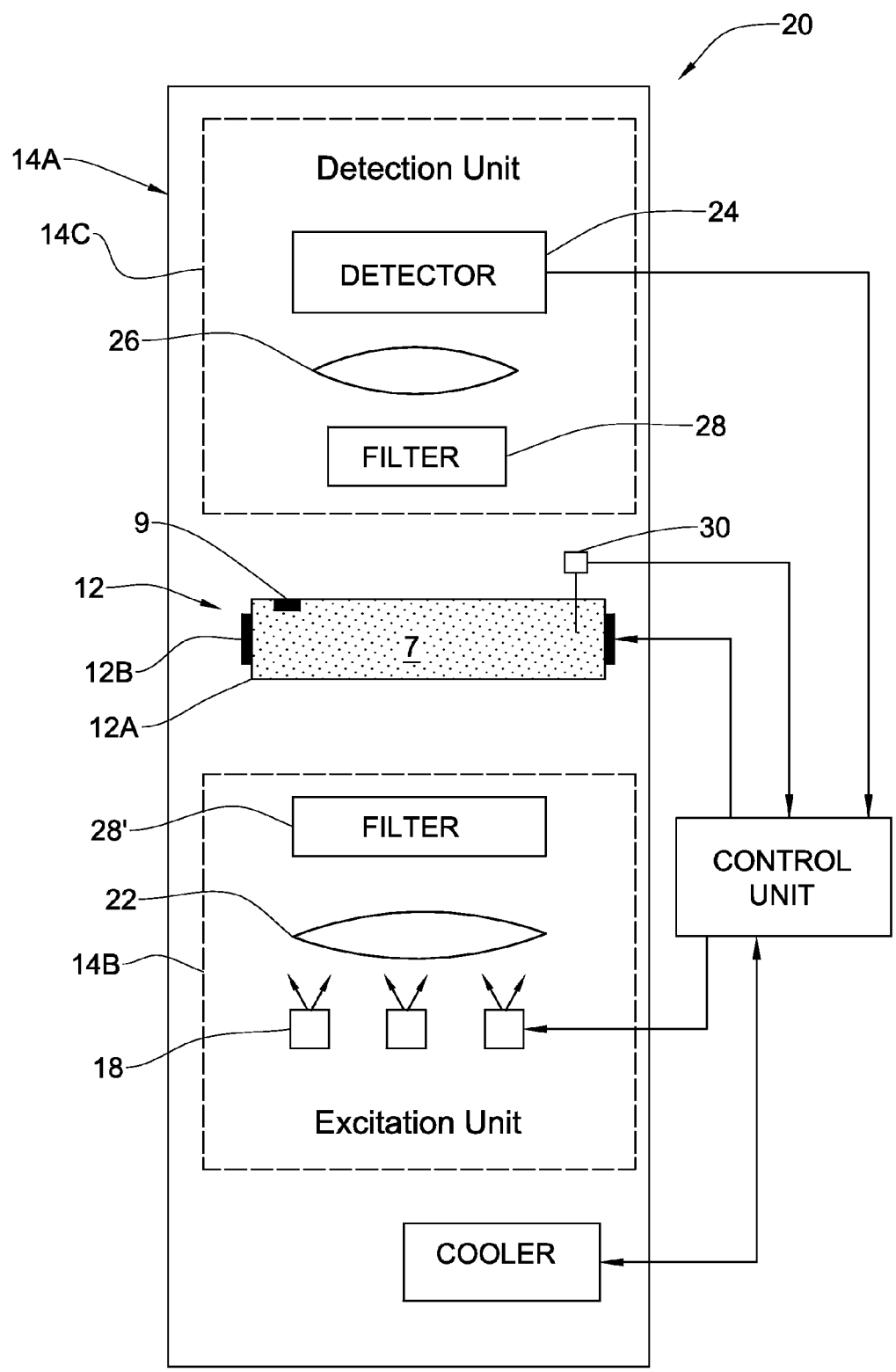
FIG. 3 more specifically illustrates one example of the configuration of the system of FIG. 2D.

Reference is made to FIG. 3 where the monitoring unit 14 integrated with the separation unit 12 is shown, altogether forming a real-time monitoring system 20 according to the present invention. The monitoring unit 14 includes an excitation unit 14B and a detection unit 14C. In the present example, the excitation unit 14B is positioned under the separation unit 12, and thus excitation of material in container 12A (sample 9 in matrix medium 7) is performed through the bottom of the container 12A. Other spatial configuration may be applied as well and will be described further below. The excitation unit 14B includes one or more excitation source, generally at 18. In the present example, several radiation sources 18 are used, e.g., UV sources. Excitation source (s) 18 may be stationary mounted or mounted for movement with respect to the container. The excitation unit may include several radiation sources operating in different spectral ranges, or a broadband source and one or more spectral filter, generally at 28 and 28'. The configuration may be such that the excitation unit is shiftable between its different operational positions so as to apply the desired energy source or the desired filter in the monitoring procedure. In order to ensure uniform illumination of the matrix medium 7, appropriate optical means are used in the excitation unit 14B, such as condensers or field lens 22. Also, back reflectors may be utilized being mounted behind the excitation source 18, thus back reflecting the emitted radiation towards the matrix medium 7.

The detection unit 14C includes a detector 24 and a lens arrangement 26 that collects the radiation response coming from the matrix medium with the sample and focuses the collected radiation onto the detector 24. The latter may be CMOS or CCD detector. The detection unit 14C may also include a suitable spectral filter assembly 28, which may a single filter or multiple filter assembly operable to selectively locate a desired one of the filters in the optical path of the radiation response coming from the container. In the present example, the detection unit is designed as an imaging channel. It should however be understood that it may be designed to define a visual channel, as described above.

The system 10 may be configured to allow for monitoring the separation process. This is accomplished by sensors mounted in various places within the system. For example, a temperature sensor 30 may be used being installed within or proximate to the matrix medium 7 and connected to the control unit 16. Additional sensors, such as humidity sensor, can be used as well. Also preferably provided in the system are mechanical or thermoelectrical cooling means such as ventilator 32. The temperature of the matrix medium 7 can be determined by the imaging detector 24 while obtaining an IR image of the surface of the medium. Such an IR image can be captured by an IR CCD and analyzed by the control, unit. Additional sensors may be used being mounted in or in the vicinity of the monitoring unit 14, such as temperature and/or humidity sensor to monitor the environmental conditions which are relevant to the system operation.

It should also be noted that the excitation source may be operated continuously or in timely separated sessions. This depends on the type of the matrix medium used, the type of exciting radiation, and also on the parameters of the separation process (e.g., voltage). For example, data coming from the temperature sensor may be used to appropriately shift the excitation source between its operative and inoperative positions.

Figure 4:
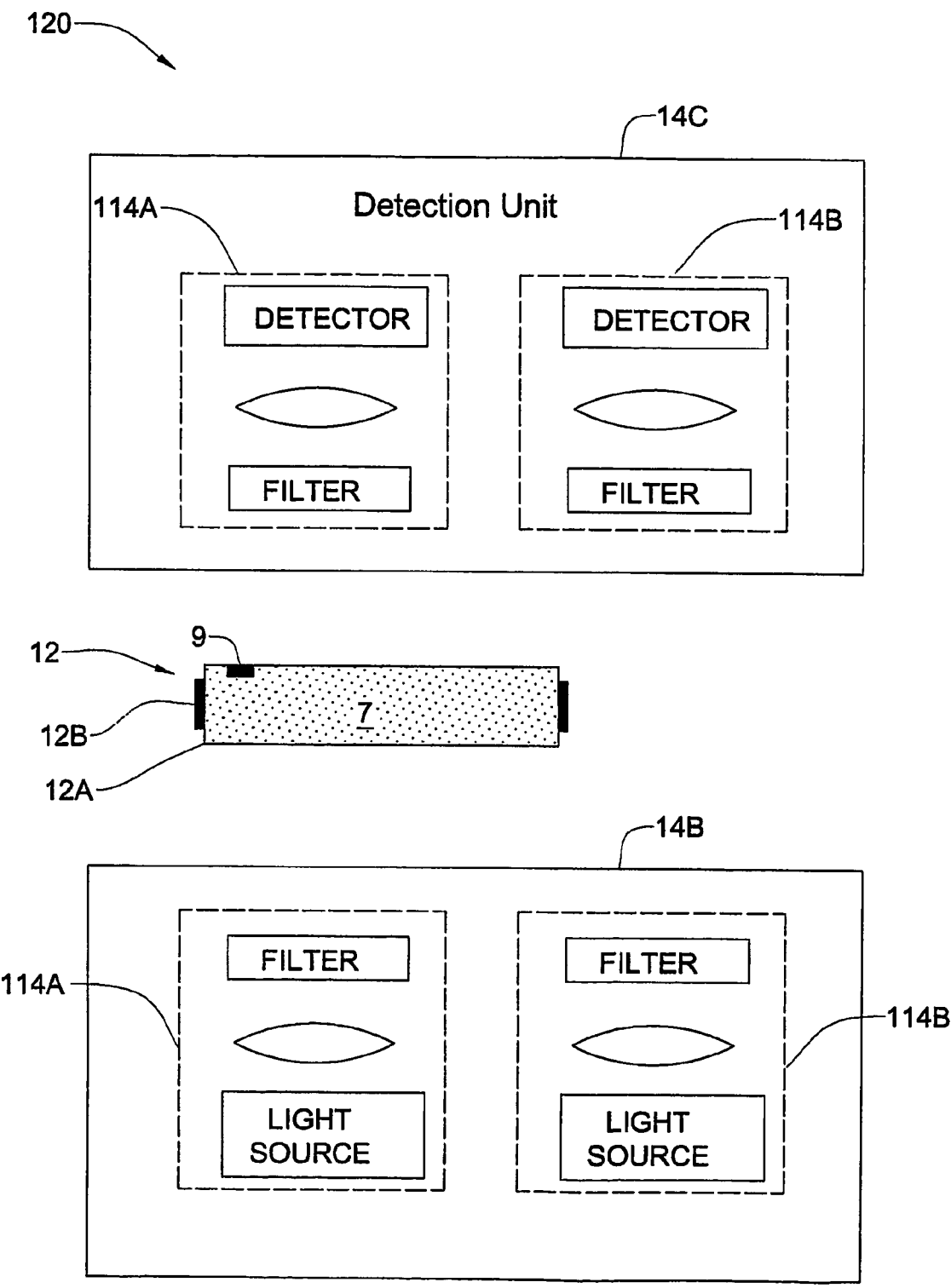
FIG. 4 illustrates another example of the configuration of the system of FIG. 2D.

FIG. 4 illustrates another example of a monitoring system of the invention, generally designated 120. To facilitate understanding, the same reference numbers are used for identifying components that are common for all the examples of the invention. System 120 utilizes multiple (generally at least two) monitoring sub-units 114A and 114B accommodated in a common housing 14A configured to be integrated with a separation unit 12. Each of the sub-units is configured as excitation/detection assembly formed by an excitation unit and a detection unit. Each of the excitation/detection assemblies is mounted for movement with respect to the separation unit 12 between its operative and inoperative position. The components of each of sub-unit are specifically chosen for certain excitation process. For example, sub-unit 114A is designed for UV excitation/detection, and sub-unit 114B is designed for operating in IR spectrum. The system 120 enables monitoring different mediums with different excitation processes. In addition it enables to monitor single medium with at least two different excitation processes. This might be useful, when a sample under investigation is composed of different molecules which cannot be all together detected by single excitation process (e.g., UV or IR radiation). Therefore, by successively applying different excitation/detection processes, all the molecules in the sample and/ or their position in the matrix medium can be identified. The common control unit 16 successively operates the sub-units to enable obtaining data indicative of all the required information about the sample. The control unit then processes the so-obtained data obtained received from two analyzing sub-units, and establishes one "image" in which all the molecules are present with their certain amounts and positions.

Figure 5A:
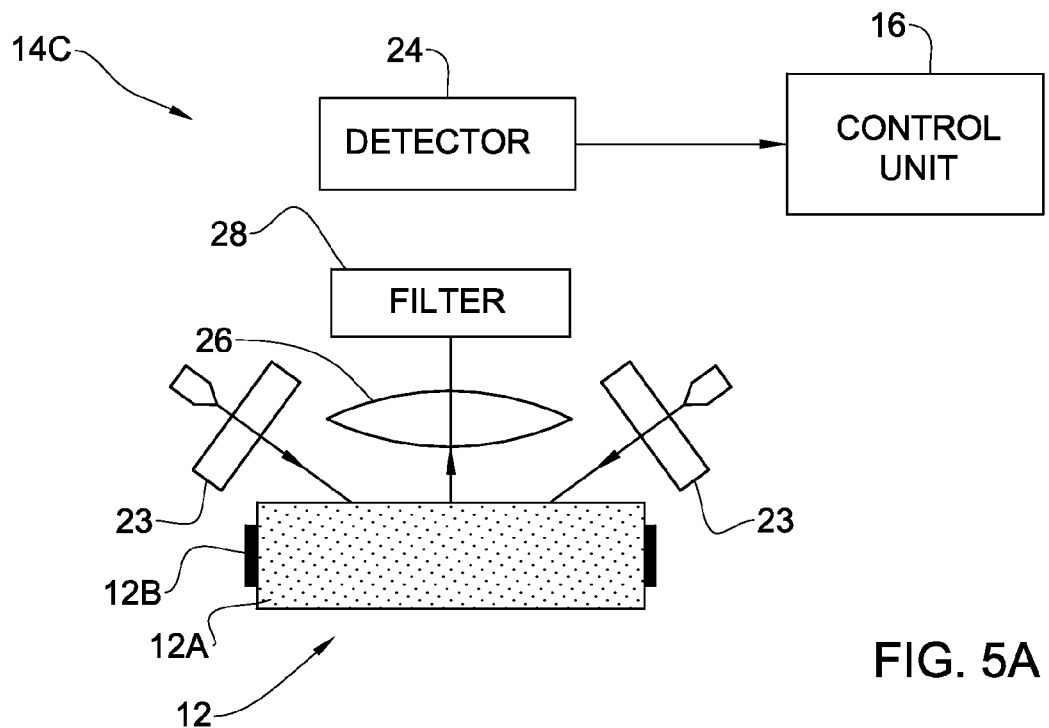
FIGS. 5A and 5B illustrate two more examples of the configuration of the system of FIG. 2D.
Figure 5B:
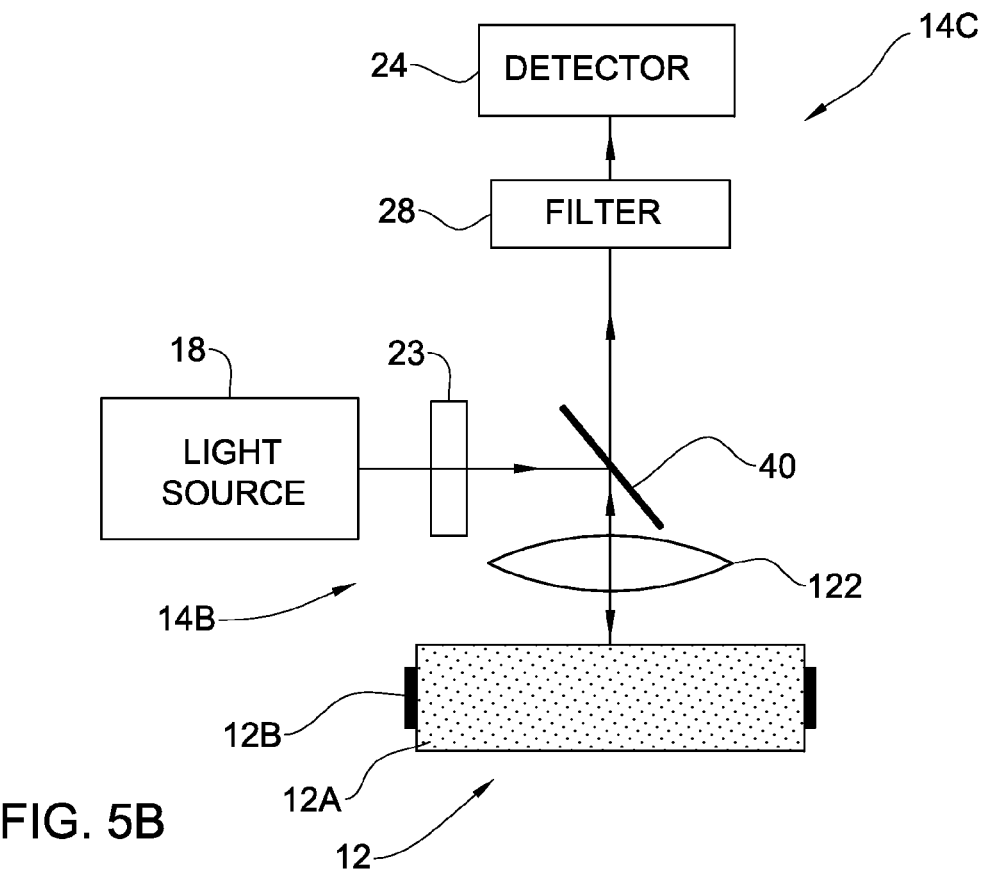

Reference is made to FIGS. 5A and 5B showing two more examples, respectively, of a monitoring system of the present invention. In both examples, a monitoring unit 14 is configured such that the excitation unit 14B and the detection unit 14C are positioned at the same side of the container 12A of the separation unit 12, the monitoring unit thereby operating in the reflection mode.

In the example of FIG. 5A, the excitation unit 14B comprises one or more excitation source 18, for example radiation sources operating in different spectral regions, e.g., short wavelengths ($\lambda_1$<190 nm) and longer wavelengths (190 nm<$\lambda_2$<300 nm), and/or radiation sources associated with different spectral filters 28. The filters 28 may be shiftable between their operative position being in the optical path of exciting radiation, and inoperative position being outside this optical path.

In the example of FIG. 5B, the excitation unit 14B and detection unit 14C utilize common radiation directing optics including a focusing/collecting lens 122 and a beam splitter 40. The excitation source 18 generates exciting radiation, which is reflected from the beam splitter 40 and directed by lens 22 onto the container 12A of the separation unit 12 so as to substantially uniformly illuminate the surface of the matrix medium 7 in the container. Radiation returned (reflected/scattered) from the illuminated region is collected by the same lens 23 and transmitted through the beam splitter 40 to the detector 24. The beam splitter thus spatially separate the exciting and excited radiation parts.

Figure 6:
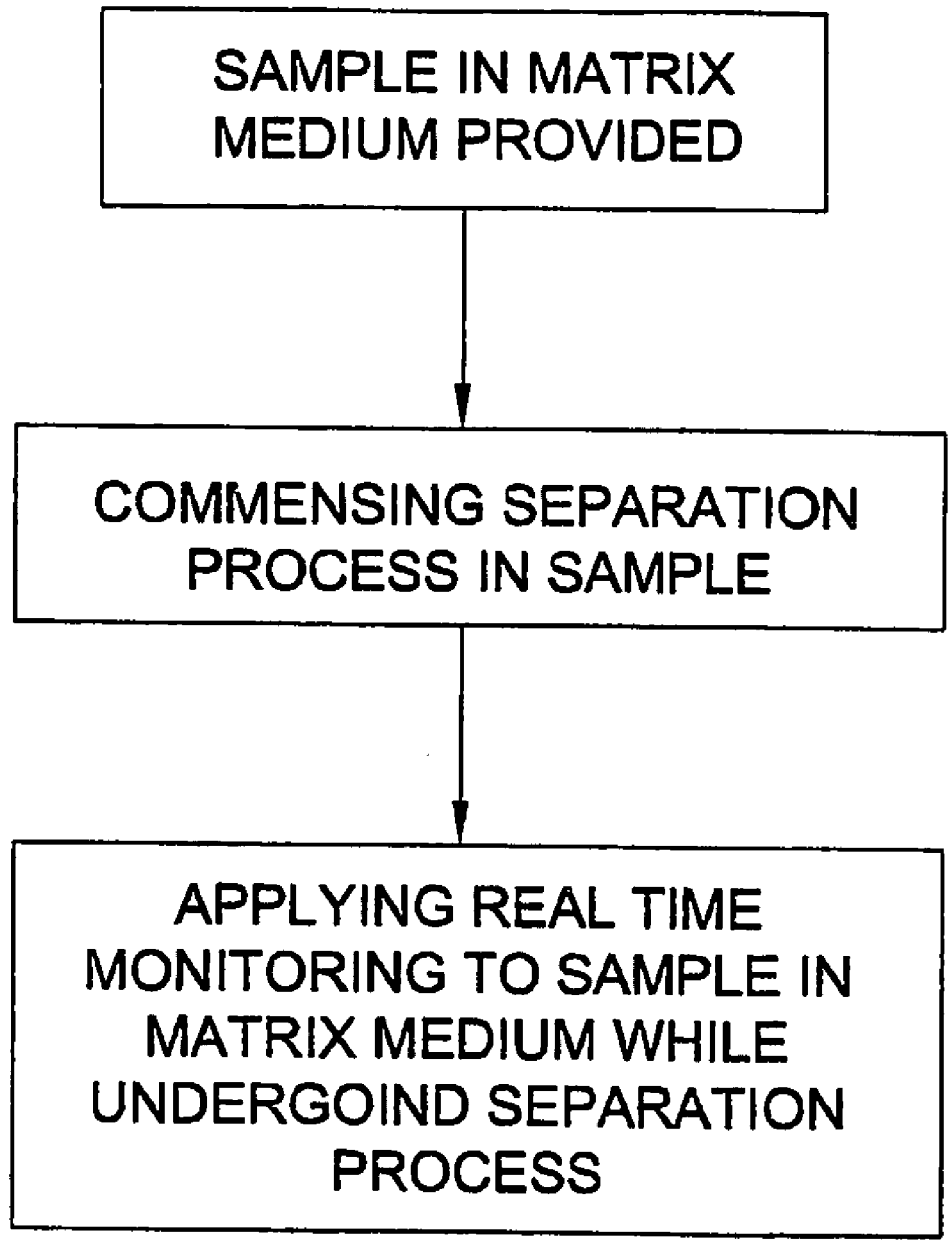
FIG. 6 is flow chart of a method of the invention for real time monitoring of the separation process.

Thus, the present invention provides for real time monitoring the separation process and/or the separation results. The main steps in the method of the invention are shown in FIG. 6. A sample under investigation is embedded in a matrix medium located in an appropriate container. The separation process is commenced. Monitoring process is applied, which may be carried out continuously during the separation process, in timely separated sessions, or applied once after a predetermined period of duration of the separation process, all without a need for transferring the container or separation unit from the separation region to a remote location of an analyzing system. It should be understood that the term "monitoring" signifies any detection of any result of the separation process (e.g., the spatial separation of the molecule), or any related operational state or condition (e.g., velocity of separation, environmental conditions in matrix media), as well as optionally analyzing such detection.

Monitoring is used in accordance to various embodiments. Monitoring can be operated by the control unit (16 in FIG. 2D) before, during, in between or after the separation process is stopped. It can also be operated continuously, periodically, with interruptions, or at a predetermined times, all with respect to the separation process.

Monitoring may be operated periodically, starting before the separation process commences, and then during its operation. Such monitoring is aimed at identifying and controlling the spatial separation of smaller molecules. In order to prevent its early arrival at the edge of the matrix media, the monitoring period is determined accordingly (e.g., based on the library data or any other relevant data). The data indicative of detected images (analysis results) of the matrix media with the sample are continuously processed by the control unit. The processing is based on pre-determined algorithms and conditions. The conditions may include an operation parameter such as certain position along the matrix media where molecules should be detected at, e.g., the end-point of separation lane. The control unit then periodically operates the monitoring, and upon identifying such a predetermined condition (e.g., arrival of molecules to the predetermined edge of the matrix media), operates to stop the separation process. This may prevent the failure of the separation process due to 'escape' of smaller molecules from the matrix media.

A closed-loop feedback control may be applied over the separation process. The user or the control unit, based on the monitored data and its analysis, determines the durations by which monitoring is to be operated and which parameters and conditions are to be detected and analyzed. Moreover, these parameters/conditions may change (reduce or enlarge) the values of the process parameters such as electric field intensity and/or its duration.

Figure 7A:
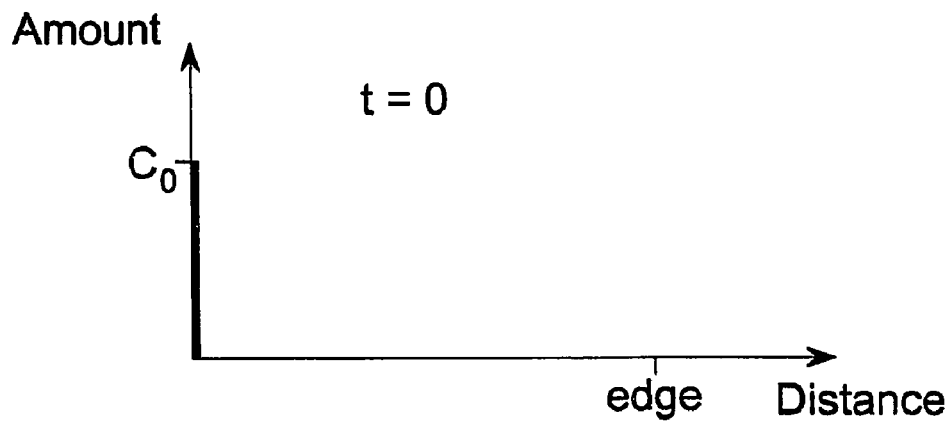
FIGS. 7A to 7C illustrate the principles of the present invention of the real time monitoring of the separation process.
Figure 7B:
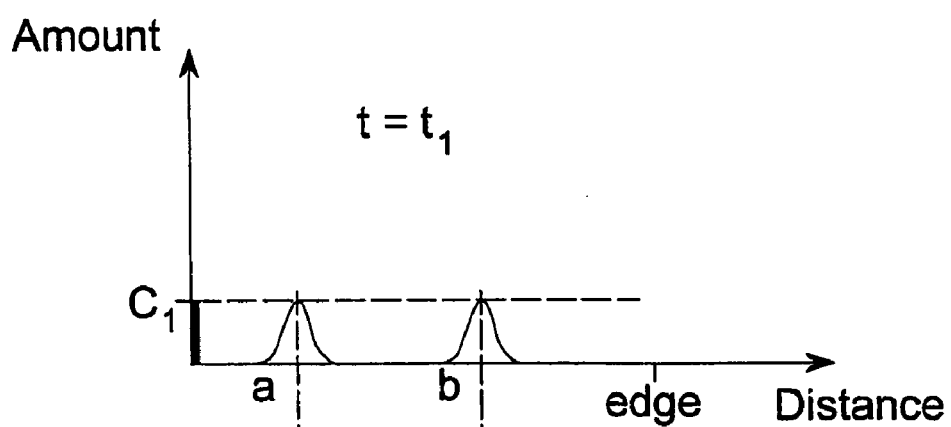
Figure 7C:
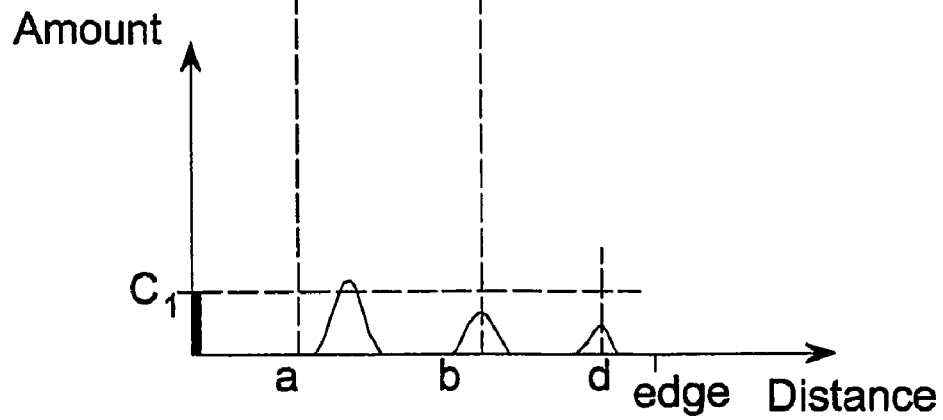

For example, beside the position of molecules, their spatial distribution is detected as illustrated in FIGS. 7A-7C. Here, the x-axis is the horizontal distance from the point where the sample is introduced into the matrix medium, y-axis is the amount of molecules (mass). Before the separation process is commenced, an image of the matrix medium is acquired and analyzed by the control unit. Analysis is conducted by converting the light distribution in the captured image to molecules mass at certain positions. Transformation is done based on predetermined calibration curve(s). As shown in FIG. 7A, prior to the separation, $C_0$ amount of molecules is found only at '0' position, i.e., at the sample well. Then, as shown in FIG. 7B, after a certain time period $t_1$ from the start of the separation process, another image is acquired and analyzed similarly. As shown, two new mass distributions a and b appear, amounting to $C_1$. At this point of time, either the user manually, or the control unit automatically, may change the separation process parameter in order to affect the separation process and thus cause new results. For example, in this run, the electric potential was increased, and it was found that mass distribution a and b will move away of the '0' point, and mass distribution b will split by forming new mass distribution d as shown in FIG. 7C. Thus, new steps and evolutions of the separation process can be detected with the aid of the monitoring. Such monitoring enables Fully Real Time automated documentation and report of the separation procedure.

As indicated above, the temperature of the matrix medium may be continuously or periodically detected, during the separation process and/or during the operation of the excitation unit. From this real time detected temperature, short and long term data can be obtained as well as optimal operational parameters. For example, if it is found that after excitation the temperature increased above a predetermined level, the control unit will operate a cooling unit more intensively during the next excitation cycle. Additionally, or alternatively, if it is found that humidity of the matrix medium decreased under a predetermined level, the control unit will operate to effect increment of humidity in the separation unit, or if such predetermined level signifies irreversible damage to separation process, the process will be stopped. Such analyzed events are stored and long term optimal operation parameters can be determined. This will serve as part of the library to be described later.

The monitoring process may be performed manually by the user. The user can directly observe the matrix media, as described above. Before the user observes the matrix medium, appropriate protection means are inserted manually or preferably, automatically, into the optical path to protect the user's eyes and body from exciting/excited radiation. Such protecting means includes for example a UV filter and inhalation filter to prevent toxic substance from entering the user's respiratory system. The user may observe the matrix medium when required or according to a predetermined timetable and subject to allowed interruptions to the separation process. If the user identifies problematic conditions, or existence of predetermined conditions which are to be detected, he can stop the separation process completely or change any operational parameter of the process, as the case may be. For example, the user might find a too fast molecule advancement, in which case he can reduce the voltage across the matrix media.

The technique of the present invention provides for creating a special library aimed at automatically recognizing and identifying the sample contents. Automatic recognition and identification is performed by means of numbers, barcodes, color, shape, RF-ID or any other marking on the sample substance that is to undergo the separation process. The library contains information of two types: (a) a-priori available information and (b) post-monitoring information. The type (a) information includes (1) general data about separation processes such as existing separation kits and procedures, and (2) general information about materials to be used with relation to separation processes such as available dyes, flourofores, flourochromes or any available markers to be used in a separation method. It may also include data provided by the manufacture of such markers. Information of type (b) includes data about practical and actual performance of separation processes and running of the media/sample, resulted from monitoring of separation processes and what followed it (e.g., analysis results). It may include information about excitation mechanisms that were detected, emission data, and resulted filters needed for the processes, as well as data about detectors and there performance.

Figure 8:
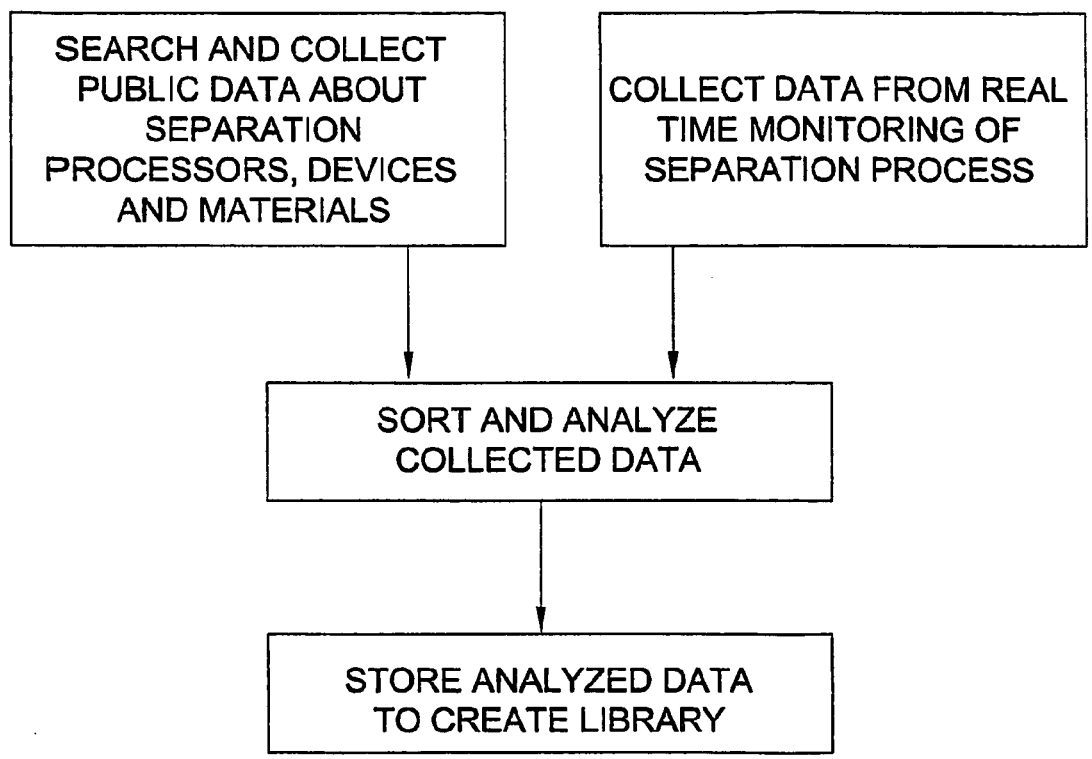
FIG. 8 is a flow chart of a method of the present invention for creating a library to be used in carrying out and/or monitoring of a separation process.

An example of a method of establishing and using the aforesaid library is shown in FIG. 8. Public data about separation processes, devices and materials used therein (aforesaid type a), is searched for and collected. Such search and collection is signified "public collection". Data is obtained from any public free or restricted sources, published, or available in any accessible media (e.g., journals, books, cyberspace). In parallel to public collection, in connection or with no connection to it, or consequently to it, data resulted from real-time controlled separation system of the present invention is collected (data of aforesaid type b). Data of the two types are sorted and analyzed in order to establish a comprehensive database for the performance and operation of separation processes, and all the data required to perform optimally and/or successfully such processes. Sorting is made based on e.g., types of processes, procedures for performance of separation processes, equipment used with respect thereto, (optimal) operational parameters (e.g., temperature, humidity), and materials characteristics. It should be noted that sorting can be performed already for both types of data or any of it, during public collection and/or collection of type b data.

During analysis, the sorted data from type a and b are checked and inspected, for example its validity, errors, inaccuracies, etc. During analysis, data of type a and type b may also be compared one to another. Such comparison may result with combining data, abandoning data, or conducting further inspection or search. For example, data from markers' manufactures about markers' composition and toxicity may be combined (i.e., stored in connection to each other) to establish the library section about these markers. Data from gel manufactures about is optimal operation parameters (e.g., temperature and humidity) is compared with monitored data of such gel vs. the results of separation process. Such comparison may come with conclusion that the manufacture data is wrong or inaccurate, as well as no conclusive result, according to further inspections should be taken in order to finalize the issue. Markers excitation wavelength (data of type a) is compared after analysis with detected wavelength of such markers used in a specific separation process (data of type b).

The library establishment is completed by storing the analyzed locally (e.g., in the control unit of the monitoring system), or in a central station which is accessible to various users. Such library may be updated, changed, or corrected, continuously or per case.

The library is used "as is" in order to directly utilize information contained therein, i.e., accessed online or offline, accessed locally via the control unit of the monitoring system, or via a network or cyberspace connection. Users can apply the library automatically to there system or use it as an advisory guide line. The library can also be used to prepare reports, suggestion or any auxiliary information that is related with separation processes.

For example, if an operator meets with an unknown procedure, he can use the library search and identify data stored already in the library that best matches the unknown procedure. He may come out with complementary information as to how to perform the procedure, or results such that the procedure is not recommended or inaccurate. User who has in his disposal a matrix media, but lacking important information as to how to use this medium, can immediately search for such necessary information in the library. The data processing utility (computer system) intended for establishing such a library is an expert system capable of self learning and adjusting the library design to user profiles.

Figure 9:
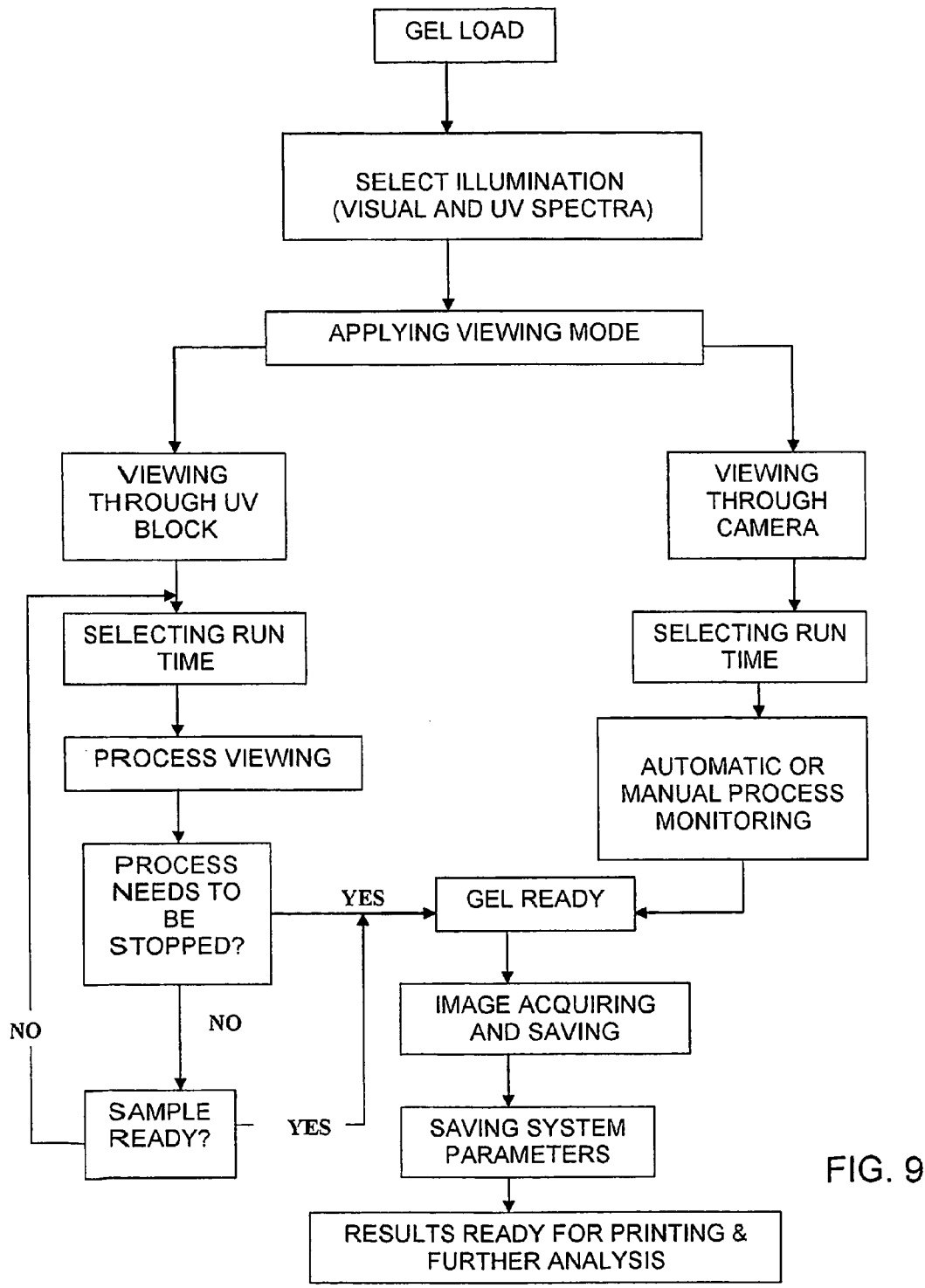
FIG. 9 exemplifies the steps of a method of operating the monitoring procedure.

FIG. 9 exemplifies the steps of a method of operating the monitoring procedure. The sample is loaded in the separation unit. The monitoring unit is configured to allow selection of appropriate illumination (exciting field), e.g., visual spectrum (e.g., monochromatic light, e.g., white light) or UV spectrum. Then, the monitoring unit is operated to carry out a viewing mode using the selected illumination, which in the present example includes both viewing through UV block and through a camera. Both of the viewing modes include selection of an appropriate run time. Considering the UV monitoring, upon the run time is selected, the process is viewed, and a decision is made as to whether to stop the process. If the process is to proceed, the control unit then "decides" whether the sample is ready, and if not selects another run time. If the process is to be stopped or if the sample is ready, then gel is considered ready. Considering the camera based viewing mode, the process is monitored automatically or manually until the gel is ready. Then, common for both viewing modes, images are acquired and saved in a memory of the control unit; and the corresponding system parameters are also saved. The results are thus ready for printing and further analysis.

Thus, the technique of the present invention provides for real-time monitoring and analyzing the separation process.

Those skilled in the art will readily appreciate that various modifications and changes can be applied to the embodiments of the invention as hereinbefore exemplified without departing from its scope defined in and by the appended claims.

The invention claimed is:

1. A method for analyzing a sample contained in a matrix medium, the method comprising:
providing a monitoring system configured to be integrated with a separation unit, the separation unit comprising
a container containing the sample embedded in the matrix medium, and
a source of an external exciting field capable of inducing the separation process in the sample, the separation process consisting of spatial separation of molecules of different molecular weights in the sample; and
applying real time optical monitoring to the sample while undergoing the separation process in a separation process environment that provides for spatial separation of molecules of different molecular weights in the sample, the optical monitoring comprising
exciting the sample with the external exciting field,
detecting a radiation response of the sample to the external exciting field,
analyzing the response detected in real time,
monitoring one or more conditions of the matrix medium in which the sample is embedded and parameters of the separation process, and
providing closed-loop feedback control of the separation process to enable variance of the one or more condition and parameters to provide optimal parameters for the separation process, the one or more conditions of the matrix medium comprising a humidity condition of the matrix medium, and the parameters of the separation process comprising an intensity, duration, and direction of an applied electrical field within the separation process environment.

2. The method of claim 1, wherein the monitoring is applied continuously during the separation process.

3. The method of claim 1, wherein the monitoring is applied in timely separated sessions during the separation process.

4. The method of claim 3, wherein the duration of the time session is defined by the one or more conditions of at least one of the sample and the matrix medium in which the sample is embedded.

5. The method of claim 3, wherein the duration of the time session is defined by the parameters of the separation process.

6. The method of claim 1, wherein the monitoring is applied during a predetermined time period of the separation process.

7. The method of claim 6, wherein the predetermined time period is defined so as to identify molecules having different molecular weights in the sample.

8. The method of claim 6, wherein the predetermined time period is defined by the conditions of at least one of the sample and the matrix medium in which the sample is embedded.

9. The method of claim 6, wherein the predetermined time period is defined by the parameters of the separation process.

10. The method of claim 1, wherein the external exciting field is selected so as to enable excitation of a specific molecule in the sample.

11. The method of claim 1, wherein the monitoring further comprises providing data regarding an optimal duration of the separation process, thereby enabling stoppage the separation or allowing the separation to proceed.

12. The method of claim 1, wherein the monitoring comprises providing data regarding optimal parameters of the separation process, thereby allowing for variance of the separation process parameters.

13. The method of claim 1, wherein the parameters comprise a parameter of the external field commencing the separation process.

14. The method of claim 1, wherein the detecting of the radiation response comprises image acquisition.

15. The method of claim 14, wherein the detecting comprises visual observation.

16. The method of claim 15, comprising providing a filter assembly in an optical path of the radiation response.

17. The method of claim 1, wherein the detecting comprises visual observation.

18. The method of claim 17, further comprising providing a filter assembly in an optical path of the radiation response.

19. The method of claim 18, wherein the filter assembly comprises a filter configured to lock UV radiation and to transmit other spectral components.

20. The method of claim 1, comprising configuring the monitoring system to be integrated with a molecule separation unit, the molecular separation unit comprising the container for carrying the sample embedded in the matrix medium, and the source of an external field commencing the separation process.

21. The method of claim 1, further comprising monitoring the separation process.

22. The method of claim 1, wherein the monitoring comprises imaging the medium in which the sample is embedded.

23. The method of claim 22, wherein the imaging comprises irradiating the medium by exciting radiation of at least one predetermined wavelength range, detecting a radiation response of the medium, and generating data indicative thereof.

24. The method of claim 22, wherein the imaging comprises visual observation of the sample in the matrix medium.

25. The method of claim 1, further comprising carrying out public collection of data, analyzing the public collection data and data indicative of the monitoring results, generating data indicative of analysis results, and storing the analyzed data.

26. The method of claim 25, wherein the analyzed data is used to establish a library.

27. The method of claim 1, further comprising establishing a library comprising information regarding various parameters of the separation process and media used therein, thereby enabling use of the library for the real time monitoring of the separation process while the sample is located within the separation process environment and affecting performance of the separation process.

28. The method of claim 27, wherein the establishing of the library comprises
searching and collecting data about separation processes,
collecting data resulted from real time controlled separation processes,
sorting and analyzing the collected data and generating analyzed data indicative thereof,
storing the analyzed data.

29. The method of claim 28, wherein the data about the separation processes comprises data about devices and materials used therein.

30. A system for use in analyzing a sample, the system comprising:
a separation unit comprising a container configured to carry matrix medium in which the sample is embedded;
a source of an external field configured and operable to commence a separation process consisting of spatial separation of molecules of different molecular weights in the sample;
a humidity sensor configured to identify a humidity condition of the matrix medium in which the sample is embedded;
an optical monitoring unit comprising
an excitation unit generating an exciting field to be applied to a substance in the separation unit to thereby cause a response of the substance to the exciting field, and
a detection unit for detecting the response and generating data indicative thereof; and
a control unit connectable to the monitoring unit and operable to process data indicative of the monitoring results,
the monitoring unit being configured to be integrated with the separation unit, and the control unit being connectable to the separation unit and configured and operable to enable real time monitoring of the separation process to affect operation of the separation unit based on the processing results, the real time monitoring comprising a closed-loop feedback control of the separation process to enable variance of humidity conditions and parameters of the separation process to provide optimal parameters for the separation process, the parameters of the separation process to be controlled comprising an intensity, duration, and direction of an applied electrical field within the separation process environment.

31. The system of claim 30, wherein the monitoring unit is configured to be attachable to the separation unit.

32. The system of claim 30, wherein the monitoring unit is configured to be mountable on the separation unit.

33. The system of claim 30, wherein the monitoring unit is configured to incorporate the separation unit thereinside.

34. The system of claim 30, wherein the monitoring unit further comprising a housing configured to provide a dark room environment for the sample located therein.

35. The system of claim 30, wherein the excitation unit comprises at least one source of electromagnetic radiation, and the detection unit comprises at least one light detector.

36. The system of claim 30, wherein the detection unit is configured for visual observation of the inside of the container.

37. The system of claim 35, wherein the detection unit is configured for acquiring images of the inside of the container.

38. The system of claim 37, wherein the detection unit comprises an imaging detector shiftable between its operative and inoperative position, being respectively in and out of optical path of the radiation response.

39. The system of claim 36, wherein the detection unit comprises a filter configured for blocking predetermined radiation spectrum and transmitting other spectral components.

40. The system of claim 39, wherein the filter is mounted to be shiftable between its operative position being in the optical path of the radiation response and inoperative position being outside said optical path.

41. The system of claim 30, wherein the detection unit is configured for acquiring images of the inside of the container.

42. The system of claim 41, wherein the detection unit comprises a filter configured for blocking predetermined radiation spectrum and transmitting other spectral components.

43. The system of claim 42, wherein the filter is mounted to be shiftable between its operative position being in the optical path of the radiation response and inoperative position being outside said optical path.

44. The system of claim 42, wherein the detection unit comprises an imaging detector shiftable between its operative and inoperative position, being respectively in and out of optical path of the radiation response.

45. The system of claim 30, wherein the source of the external field used in the separation unit is a voltage supply source operable to apply a potential difference between opposite sides of the container along at least one axis of the container.

46. The system of claim 30, wherein the monitoring unit is a two-part unit, one part being carrying the excitation unit and being mountable at one side of the separation unit, and the other part carrying the detection unit and being mountable at the opposite side of the separation unit.

* * * * *